United States Patent
Aneja et al.

(10) Patent No.: US 12,342,987 B2
(45) Date of Patent: *Jul. 1, 2025

(54) DEVICES, SYSTEMS, AND METHODS FOR PROVIDING SEALABLE ACCESS TO A WORKING CHANNEL

(71) Applicant: BOSTON SCIENTIFIC MEDICAL DEVICE LIMITED, Galway (IE)

(72) Inventors: Harchetan S. Aneja, Amritsar (IN); Amit Bharos, Jabalpur (IN); Swami Upadhyay, Raipur (IN); Boopathi Rajarathnam, Salem (IN)

(73) Assignee: BOSTON SCIENTIFIC LIMITED, St. Michael (BB)

( * ) Notice: Subject to any disclaimer, the term of this patent is extended or adjusted under 35 U.S.C. 154(b) by 238 days.

This patent is subject to a terminal disclaimer.

(21) Appl. No.: 17/948,408

(22) Filed: Sep. 20, 2022

(65) Prior Publication Data
US 2023/0020326 A1    Jan. 19, 2023

Related U.S. Application Data

(63) Continuation of application No. 16/671,786, filed on Nov. 1, 2019, now Pat. No. 11,478,233.
(Continued)

(51) Int. Cl.
*A61B 1/00*    (2006.01)
*A61B 1/015*    (2006.01)
(Continued)

(52) U.S. Cl.
CPC ...... *A61B 1/00137* (2013.01); *A61B 1/00064* (2013.01); *A61B 1/0011* (2013.01);
(Continued)

(58) Field of Classification Search
CPC ..... A61B 1/00137; A61B 1/015; A61B 1/018; A61B 1/0011; A61B 1/0014; A61B 1/00121
See application file for complete search history.

(56) References Cited

U.S. PATENT DOCUMENTS

| | | |
|---|---|---|
| 4,198,959 A | 4/1980 | Otani |
| 5,104,379 A | 4/1992 | Nakamura et al. |

(Continued)

FOREIGN PATENT DOCUMENTS

| | | |
|---|---|---|
| AU | 199927921 A1 | 12/1999 |
| AU | 200156987 A1 | 11/2001 |

(Continued)

OTHER PUBLICATIONS

Cook Medical—"Fusion® Wire Guide Locking Device" URL: https://www.cookmedical.com/products/esc_fswl_webds/ © Cook 2021.

(Continued)

*Primary Examiner* — Timothy J Neal
(74) *Attorney, Agent, or Firm* — Seager, Tufte & Wickhem, LLP

(57) ABSTRACT

The present disclosure relates generally to the field of medical devices. In particular, the present disclosure relates to valve configurations providing sealable access for medical instruments to a working channel, such as a working channel for an endoscope.

20 Claims, 10 Drawing Sheets

Related U.S. Application Data

(60) Provisional application No. 62/755,024, filed on Nov. 2, 2018, provisional application No. 62/768,808, filed on Nov. 16, 2018, provisional application No. 62/834,192, filed on Apr. 15, 2019, provisional application No. 62/834,201, filed on Apr. 15, 2019.

(51) Int. Cl.
*A61B 1/018* (2006.01)
*A61B 10/02* (2006.01)
*A61B 10/04* (2006.01)
*B29D 99/00* (2010.01)

(52) U.S. Cl.
CPC ........ *A61B 1/0014* (2013.01); *A61B 1/00147* (2013.01); *A61B 1/015* (2013.01); *A61B 1/018* (2013.01); *A61B 10/0275* (2013.01); *A61B 10/04* (2013.01); *B29D 99/0053* (2013.01)

(56) References Cited

U.S. PATENT DOCUMENTS

| | | | |
|---|---|---|---|
| 5,312,363 A * | 5/1994 | Ryan | A61M 39/06 604/167.04 |
| 5,743,884 A | 4/1998 | Hasson et al. | |
| 6,605,075 B1 | 8/2003 | Burdulis | |
| 7,226,411 B2 | 6/2007 | Akiba | |
| 7,473,221 B2 | 1/2009 | Ewers et al. | |
| 7,637,863 B2 | 12/2009 | Deal et al. | |
| 7,670,285 B2 | 3/2010 | Kamaya | |
| 7,670,316 B2 | 3/2010 | Windheuser et al. | |
| 7,803,107 B2 | 9/2010 | Carrillo | |
| 7,967,744 B2 | 6/2011 | Kaye et al. | |
| 8,012,129 B2 | 9/2011 | Bettuchi et al. | |
| 8,152,774 B2 | 4/2012 | Pasqualucci | |
| 8,231,525 B2 | 7/2012 | Cohen et al. | |
| 8,333,693 B2 | 12/2012 | Hamazaki | |
| 8,343,041 B2 | 1/2013 | Byers et al. | |
| 8,480,570 B2 | 7/2013 | Tinkham et al. | |
| 8,702,596 B2 | 4/2014 | Kaye et al. | |
| 8,753,264 B2 | 6/2014 | Carrillo, Jr. et al. | |
| 8,974,377 B2 | 3/2015 | Yamane | |
| 9,089,261 B2 | 7/2015 | Greenburg et al. | |
| 9,101,738 B2 | 8/2015 | Eden | |
| 9,131,831 B2 | 9/2015 | Byers et al. | |
| 9,149,173 B2 | 10/2015 | Scopton et al. | |
| 9,566,145 B2 | 2/2017 | Trainor et al. | |
| 9,622,776 B2 | 4/2017 | Oberlaender et al. | |
| 9,955,998 B2 | 5/2018 | Kleyman | |
| 9,986,895 B2 | 6/2018 | Meloul | |
| 2005/0171402 A1 | 8/2005 | Cohen et al. | |
| 2006/0195117 A1 | 8/2006 | Rucker et al. | |
| 2007/0238928 A1 | 10/2007 | Maseda et al. | |
| 2007/0244356 A1 | 10/2007 | Carrillo et al. | |
| 2007/0282166 A1 | 12/2007 | Ayala et al. | |
| 2007/0293719 A1 | 12/2007 | Scopton et al. | |
| 2008/0194913 A1 | 8/2008 | Tinkham et al. | |
| 2008/0294113 A1* | 11/2008 | Brockmeier | A61B 17/3498 604/167.06 |
| 2009/0005799 A1 | 1/2009 | Franer et al. | |
| 2009/0088600 A1 | 4/2009 | Meloul | |
| 2009/0287052 A1 | 11/2009 | Amos et al. | |
| 2010/0081878 A1 | 4/2010 | Byers et al. | |
| 2010/0087705 A1 | 4/2010 | Byers et al. | |
| 2010/0087710 A1 | 4/2010 | Weldon et al. | |
| 2010/0240956 A1 | 9/2010 | Secrest et al. | |
| 2012/0071713 A1* | 3/2012 | Kaye | A61B 1/00137 600/104 |
| 2013/0150793 A1 | 6/2013 | Beissel et al. | |
| 2014/0187866 A1 | 7/2014 | Kaye et al. | |
| 2015/0190170 A1 | 7/2015 | Frederick et al. | |
| 2016/0206859 A1 | 7/2016 | Eden | |
| 2017/0202438 A1 | 7/2017 | Ogi | |
| 2017/0319828 A1 | 11/2017 | Doepker et al. | |
| 2018/0310806 A1 | 11/2018 | Gavalis et al. | |
| 2019/0046016 A1 | 2/2019 | Rajarathnam et al. | |
| 2019/0142463 A1 | 5/2019 | Zhu | |
| 2020/0138272 A1 | 5/2020 | Neelamegam et al. | |
| 2020/0138273 A1 | 5/2020 | Neelamegam et al. | |
| 2020/0138274 A1 | 5/2020 | Aneja et al. | |
| 2020/0138277 A1 | 5/2020 | Neelamegam et al. | |
| 2020/0138419 A1 | 5/2020 | Aneja et al. | |

FOREIGN PATENT DOCUMENTS

| | | |
|---|---|---|
| AU | 759421 B2 | 4/2003 |
| CN | 105816208 A | 8/2016 |
| CN | 205697867 U | 11/2016 |
| EP | 1997444 A2 | 12/2008 |
| EP | 1406691 B1 | 1/2010 |
| EP | 2505119 A1 | 10/2012 |
| EP | 2564758 A1 | 3/2013 |
| EP | 2574271 A1 | 4/2013 |
| EP | 2574271 B1 | 11/2014 |
| JP | S6129703 U | 2/1986 |
| JP | 2001104315 A | 4/2001 |
| JP | 2005080867 A | 3/2005 |
| JP | 2008123063 A | 5/2008 |
| JP | 2009268777 A | 11/2009 |
| WO | 2005011791 A2 | 2/2005 |
| WO | 2008101286 A1 | 8/2008 |
| WO | 2009143129 A1 | 11/2009 |
| WO | 2009143137 A1 | 11/2009 |
| WO | 2018024109 A1 | 2/2018 |

OTHER PUBLICATIONS

International Search Report and Written Opinion for application No. PCT/IB2019/059411, mailed Jun. 25, 2020, 14 pages.
International Search Report for the International Patent Application No. PCT/IB2019/059404, mailed Feb. 17, 2020.
International Search Report for the International Patent Application No. PCT/IB2019/059407, mailed Feb. 2020, 11 pages.
International Search Report for the International Patent Application No. PCT/IB2019/059408, mailed Feb. 14, 2020, 12 pages.
International Search Report and Written Opinion for the International Patent Application No. PCT/IB2019/059409, mailed Feb. 13, 2020.
International Search Report and Written Opinion for the International Patent Application No. PCT/IB2019/059413, mailed Feb. 17, 2020, 10 pages.

* cited by examiner

DEVICES, SYSTEMS, AND METHODS FOR PROVIDING SEALABLE ACCESS TO A WORKING CHANNEL

CROSS-REFERENCE TO RELATED APPLICATIONS

This application is a continuation of and claims the benefit of the earlier filing date of U.S. patent application Ser. No. 16/671,786, filed on Nov. 1, 2019, which claims the benefit of priority under 35 U.S.C. § 119 to U.S. Provisional Patent Application Ser. No. 62/755,024, filed Nov. 2, 2018, and titled "Attachments for Endoscopes," U.S. Provisional Patent Application Ser. No. 62/768,808, filed Nov. 16, 2018, and titled "Internal Seal for Biopsy Cap," U.S. Provisional Patent Application Ser. No. 62/834,192, filed Apr. 15, 2019, and titled "Biopsy Cap and Biopsy Cap Housing," and to U.S. Provisional Patent Application Ser. No. 62/834,201, filed Apr. 15, 2019, and titled "Devices, Systems, and Methods For Providing Sealable Access To A Working Channel," the disclosures of which are incorporated by reference herein in their entireties and for all purposes.

FIELD

The present disclosure relates generally to the field of medical devices. such as endoscopes, endoscope assemblies, guidewires, guide tubes, introducers, and instrument caps for endoscopes, guidewires, guide tubes, and introducers. In particular, the present disclosure relates to biopsy cap configurations providing sealable access for medical instruments to a working channel, such as a working channel for an endoscope.

BACKGROUND

In endoscopic procedures, for example, medical professionals are faced with the challenge of accessing patient anatomy with medical instruments through a working channel of an endoscope while preventing undesired fluid exchange through the inlet or proximal port of the working channel and between the patient and the atmosphere. For example, bile, air, or other fluids may undesirably enter or escape the patient. Poor leakage prevention may cause unhygienic environments for the medical professional or the patient, increasing the chances of health concerns such as infection and increasing the medical professional's frustration during a procedure.

In an attempt to achieve controlled fluid exchanges, a biopsy cap in line with the working channel (e.g., attached to the inlet/proximal port of the working channel) of an endoscope may provide sealable instrument access to the working channel while restricting undesired fluids from entering or exiting. These functions may generally be inversely related, such that as it is made easier for the medical professional to pass instruments through the valve, it may be harder to prevent fluids from leaking through the valve. Conversely, a valve designed for significant leakage prevention may require additional force from a medical professional to pass medical instruments through the valve, which may be difficult for delicate instruments or for instruments having a large diameter. Additionally, as medical instruments are moved through the valve and/or locked into a position, the valve may be damaged, which may compromise leak prevention.

It is with these considerations in mind that a variety of advantageous medical outcomes may be realized by the medical devices, systems, and methods of the present disclosure.

SUMMARY

Embodiments of the present disclosure may assist generally with valve configurations providing sealable access for medical instruments to a working channel, such as a working channel for an endoscope.

In one embodiment, a device for providing reinforced sealable access to a working channel may include a tubular body having a proximal end, a distal end and a longitudinal axis. The distal end of the tubular body may be configured to be removably disposed on a proximal end of the working channel in fluid communication therewith. A substantially linear aperture may be at the proximal end of the body configured to allow one or more medical instruments to be passed therethrough and, at the same time, substantially seal against fluids from the working channel passing therethrough. A plurality of reinforcing ribs may be arrayed about the aperture to reinforce the aperture against tearing.

In various embodiments described here and otherwise, the aperture may be substantially closed when there are no medical instruments passing therethrough. The ribs may extend radially in a plane substantially transverse to the longitudinal axis. Each rib of the plurality of ribs may have a width dimension in the transverse plane and a thickness dimension in a plane substantially parallel to the longitudinal axis. One or more of the ribs may extend substantially perpendicular to the aperture. Ribs extending substantially perpendicular to the aperture may have a greater width than the width of any other of the plurality of ribs. The ribs may have a greater width and thickness as they extend radially away from the aperture. The ribs may continuously increase in width and thickness as they extend radially away from the aperture. One or more of the ribs may have a greater thickness than the thickness of one or more of the other of the ribs. The tubular body may be hollow. The ribs may be disposed on a surface internal to the hollow tubular body. The ribs may be arranged symmetrically in a circular pattern around the aperture in the transverse plane. The tubular body may comprise silicone. The device may be a biopsy cap for sealable access to the working channel of an endoscope. A force required to tear the aperture of a body having ribs may be greater than the tear force for the aperture without the ribs.

In another embodiment, a device for providing reinforced sealable access to a working channel may include a tubular body having a proximal end, a distal end and a longitudinal axis. The distal end of the tubular body may be configured to be removably disposed on a proximal end of the working channel in fluid communication therewith. A substantially linear aperture at the proximal end of the body may be configured to allow one or more medical instruments to be passed therethrough and, at the same time, substantially seal against fluids from the working channel passing therethrough. A reinforcing ridge may extend about the aperture to reinforce the aperture against tearing.

In various embodiments described here and otherwise, the body may be hollow. The ridge may be disposed on a proximal surface of the body. The ridge may be spaced away from the aperture. The ridge may be resistant to tearing. The ridge may comprise a perimeter outline about the aperture that is ellipsoidal, circular, or oval. The ridge may have a cross section in a plane parallel to the longitudinal axis that comprises a substantially half moon shape. The aperture may be substantially closed when there are no medical instruments extending therethrough.

In yet another embodiment, a device for providing reinforced sealable access to a working channel may include a tubular body having a proximal end, a distal end and a longitudinal axis. The distal end of the tubular body may be configured to be removably disposed on a proximal end of the working channel in fluid communication therewith. An aperture may be at the proximal end of the body having a first and a second end. The aperture may be configured to allow one or more medical instruments to be passed therethrough and, at the same time, substantially seal against fluids from the working channel passing therethrough. The aperture may include a reinforced pattern that extends in a plane substantially transverse to the longitudinal axis in more than one dimension.

In various embodiments described here and otherwise, the aperture may include a third end. The aperture may extend substantially linearly from the first end to a split point. The aperture may extend substantially linearly from the split point to the second end. The aperture may extend substantially linearly from the split point to the third end. The aperture may extend from the split point to the second end at an angle degree from the split point to the first end. The aperture may extend from the split point to the third end at the same angle degree from the split point to the first end. A length of the aperture extending from the first end to the split point may be smaller than a length of the aperture extending from the split point to the second end. A length of the aperture extending from the split point to the third end may be substantially the same as the length of the aperture extending from the split point to the second end. The second and the third end may each be configured to accept and substantially fix a guidewire.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment shown where illustration is not necessary to allow those of ordinary skill in the art to understand the disclosure. In the figures.

DETAILED DESCRIPTION

Figure 1:
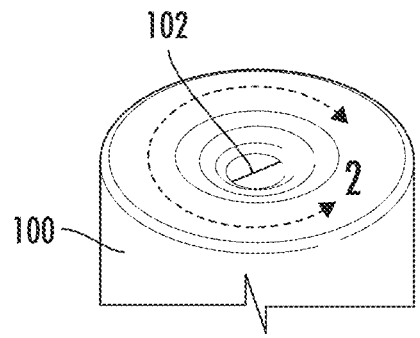
FIG. 1 illustrates an isometric view of a conventional valve.

The present disclosure is not limited to the particular embodiments described. The terminology used herein is for the purpose of describing particular embodiments only and is not intended to be limiting beyond the scope of the appended claims. Unless otherwise defined, all technical terms used herein have the same meaning as commonly understood by one of ordinary skill in the art to which the disclosure belongs.

Although embodiments of the present disclosure are described with reference to endoscopes, it should be appreciated that such devices, systems, and methods may be used with a variety of medical or other devices that include valves, working channels, ports, apertures, channels, and the like.

As used herein, the singular forms "a," "an," and "the" are intended to include the plural forms as well, unless the context clearly indicates otherwise. The terms "comprises" and/or "comprising," or "includes" and/or "including" when used herein, specify the presence of stated features, regions, steps, elements and/or components, but do not preclude the presence or addition of one or more other features, regions, integers, steps, operations, elements, components and/or groups thereof.

As used herein, the term "distal" refers to the end farthest away from the medical professional along a medical device when introducing the device into a patient, while the term "proximal" refers to the end closest to the medical professional along the medical device when introducing the medical device into a patient.

As used herein, the conjunction "and" includes each of the structures, components, features, or the like, which are so conjoined, unless the context clearly indicates otherwise, and the conjunction "or" includes one or the others of the structures, components, features, or the like, which are so conjoined, singly and in any combination and number, unless the context clearly indicates otherwise.

As used herein, the term "valve" may refer to an aperture, an opening, a slit, a slot, a seal, a seal member having multiple radial or axial protrusions, projections, or walls, either alone, in conjunction with, or integral with a biopsy cap or assembly.

All numeric values are herein assumed to be modified by the term "about," whether or not explicitly indicated. The term "about", in the context of numeric values, generally refers to a range of numbers that one of skill in the art would consider equivalent to the recited value (i.e., having the same function or result). In many instances, the term "about" may include numbers that are rounded to the nearest significant figure. Other uses of the term "about" (i.e., in a context other than numeric values) may be assumed to have their ordinary and customary definition(s), as understood from and consistent with the context of the specification, unless otherwise specified. The recitation of numerical ranges by endpoints includes all numbers within that range, including the endpoints (e.g. 1 to 5 includes 1, 1.5, 2, 2.75, 3, 3.80, 4, and 5).

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to affect such feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

Endoscopic procedures, which may include installing a biopsy cap including a valve in-line with a working channel of an endoscope, are used as context for valve embodiments described herein, but it should be understood that these and other embodiments within the scope of the present disclosure may be applicable in other disciplines, products and procedures, as mentioned above. Endoscopic procedures may include, e.g., attaching a biopsy cap to an inlet or proximal port of the endoscope working channel. The endoscope may then be inserted into a body cavity or lumen of a patient. The body cavity or lumen may then be insufflated to improve visualization and to provide a working space therein. In doing so, a positive pressure may be created in the body and in the channel. The pressure may be retained by the installed biopsy cap. At least one aperture within the biopsy cap may be configured to open, grip, and seal around one or more medical instruments that are inserted through the biopsy cap. In addition to substantially preventing the exchange of fluids across the valve(s), seal member(s), and/or aperture(s) of the cap (i.e., into and out of the working channel and/or patient), the valve(s) may "squeegee" liquids from the outer surface of the instrument as it is inserted or withdrawn. The at least one aperture is configured to substantially or completely close when unoccupied by an instrument to prevent the exchange of fluids and/or insufflation loss.

With reference to FIG. 1, an isometric view of a conventional valve is illustrated, including a biopsy cap 100. The valve 100 can be installed in-line with an inlet of a working channel. The valve 100 includes an aperture 102, which is a substantially linear, one-dimensional slit. The aperture 102 is in a substantially closed configuration without any open space between the walls of the aperture 102. The aperture 102 is ready for one or more medical instruments to be passed through the aperture 102.

Figure 2:
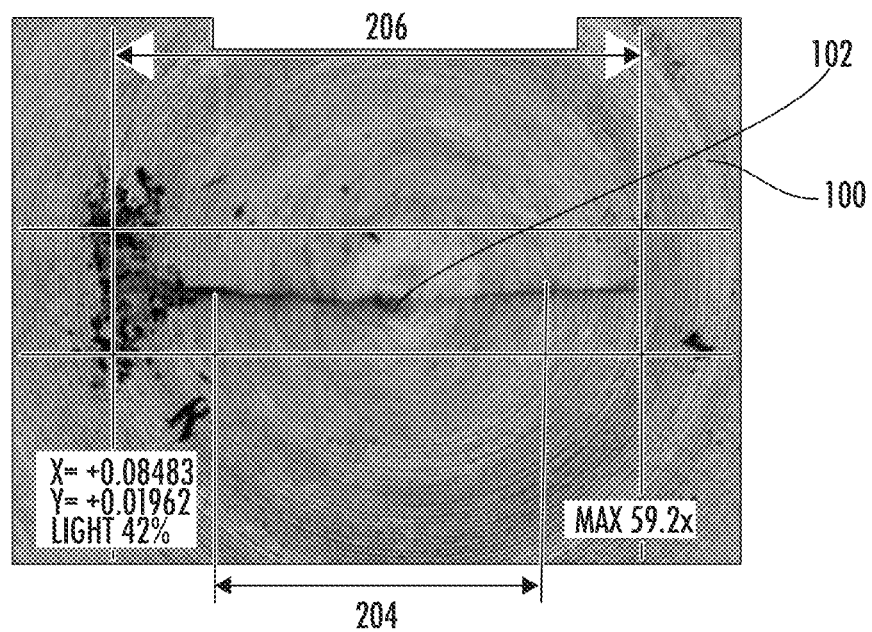
FIG. 2 illustrates a magnified view of the aperture of the used valve of FIG. 1.

With reference to FIG. 2, a magnified view of an aperture 102 of a used biopsy cap 100 of FIG. 1 is illustrated. The aperture 102 of the valve 100 extends substantially linearly across a portion of the valve 100. The aperture 102 has a length 206 after being used in the procedure, which is larger than an original length 204. During use of the valve 100, one or more medical instruments may have been inserted into the linear ends of the aperture 102, causing the aperture 102 to tear further along the valve 100 such that the length of the aperture 102 extended from the original length 204 to the enlarged length 206, decreasing the sealing strength of the valve and increasing the ease of passage through aperture 102 compared to the pre-torn aperture 102.

Figure 3A:
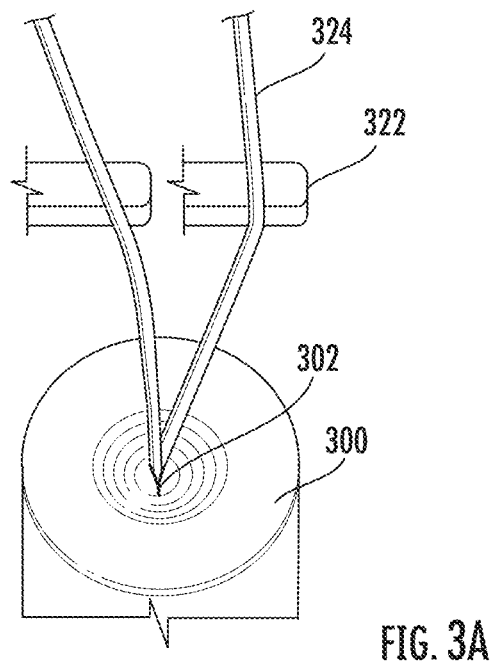
FIG. 3A illustrates a conventional valve with two guidewires extended through the valve.
Figure 3B:
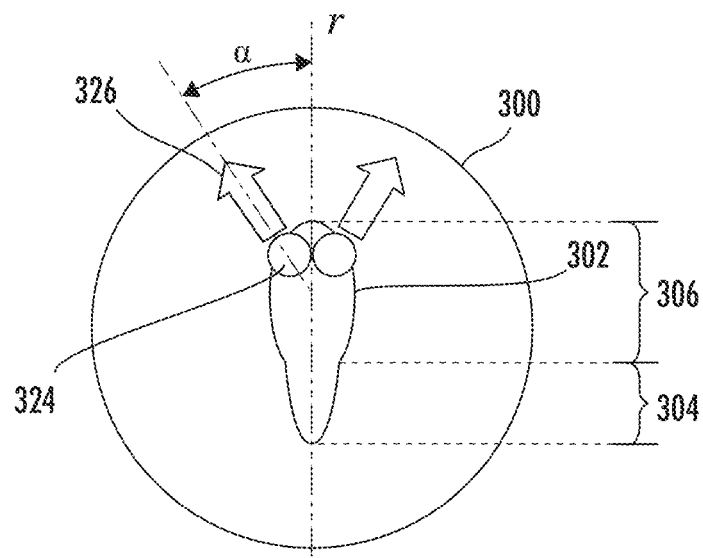
FIG. 3B illustrates a top cross-sectional view of the valve of FIG. 3A.

With reference to FIGS. 3A and 3B, a conventional biopsy cap 300 is illustrated, which includes two guidewires 324 extending through an aperture 302 according to an embodiment of the present disclosure. The guidewires 324 extend away from the aperture 302 and are guided by guide members 322. The guidewires 324 are forced against the walls of the aperture 302 generally in the direction of the vectors 326 shown in FIG. 3B. Because these vectors 326 extend in a direction that is a number of degrees a away from an axis r of the aperture 302, the aperture 302 is pulled open at least at the end of the aperture 302 with the guidewires. FIG. 3B illustrates that the guidewires 324 have torn the aperture 302 in multiple directions, causing a first portion 304 of the aperture 302 to open and a second portion 306 to open with a widening tear. The first portion 304 of the aperture 302 is undesirably open, allowing for the possible exchange of fluids through the aperture 302, while the second portion 306 is torn to a wider opening than the first portion 304, allowing for even more fluids to be exchanged through the aperture 302.

In various embodiments, a longer linear length of an aperture may be desirable to decrease the axial force required to insert and remove medical devices through the aperture when compared to a shorter linear length of an aperture. However, because a longer linear length of an aperture may be less able to prevent fluid exchanges through the aperture when compared to a shorter linear length of an aperture, a shorter linear aperture may be reinforced to accomplish both purposes, e.g. assist in allowing sealable access for instruments, while reinforcing the aperture against tearing to inhibit or prevent the exchange of fluids. For example, an aperture may have an amount of resistance to the insertion of medical devices such that at the same time there is generally a seal against the exchange of fluids across the aperture and/or such that medical devices may be wiped of fluids when being removed from the working channel and through the aperture. An exemplary amount of force necessary from a medical professional for passing one or more medical devices through an aperture, in the context of a valve used with a working channel in endoscopic procedures, may be from about 0.5 lbf to about 3.5 lbf.

In various embodiments, features and advantages of providing sealable access to a working channel, e.g., of an endoscope, may be realized in combination with a biopsy cap and biopsy cap housing. Such sealable access to a working channel, which may be reinforced, may be implemented with features throughout the disclosures of U.S. patent application Ser. No. 16/100,960, filed Aug. 10, 2018 and titled "Biopsy Cap For Use With Endoscope," United States Patent Application, filed on even date herewith and titled "Attachments For Endoscopes," United States Patent Application, filed on even date herewith and titled "Biopsy Cap And Biopsy Cap Housing," United States Patent Application filed on even date herewith and titled "Devices, Systems, And Methods For A Biopsy Cap And Housing," United States Patent Application, filed on even date herewith and titled "Internal Seal for Biopsy Cap," United States Patent Application, filed on even date herewith and titled "Devices, Systems, and Methods for Providing Sealable Access to a Working Channel," which are each incorporated by reference in their entirety and for all purposes.

Figure 4A:
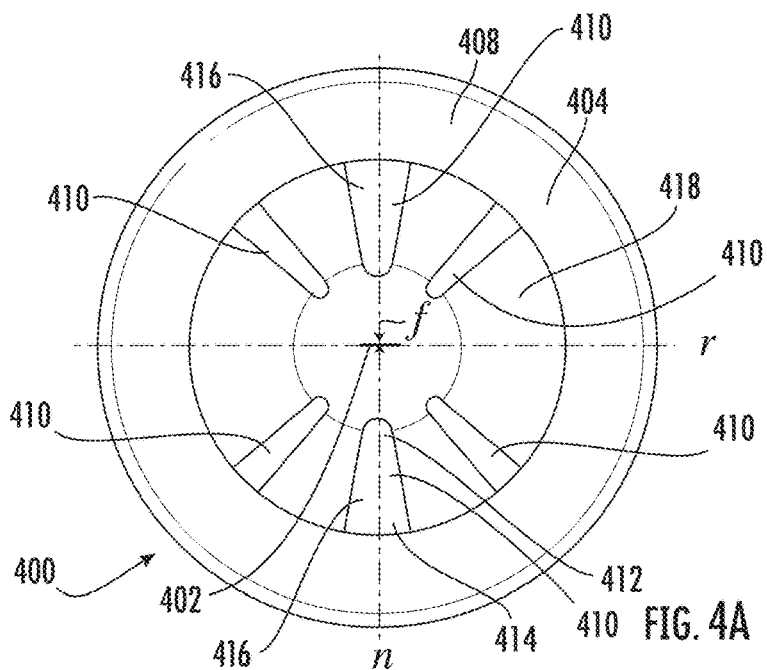
FIG. 4A illustrates a bottom view of a valve including ribs, according to an embodiment of the present disclosure.
Figure 4B:
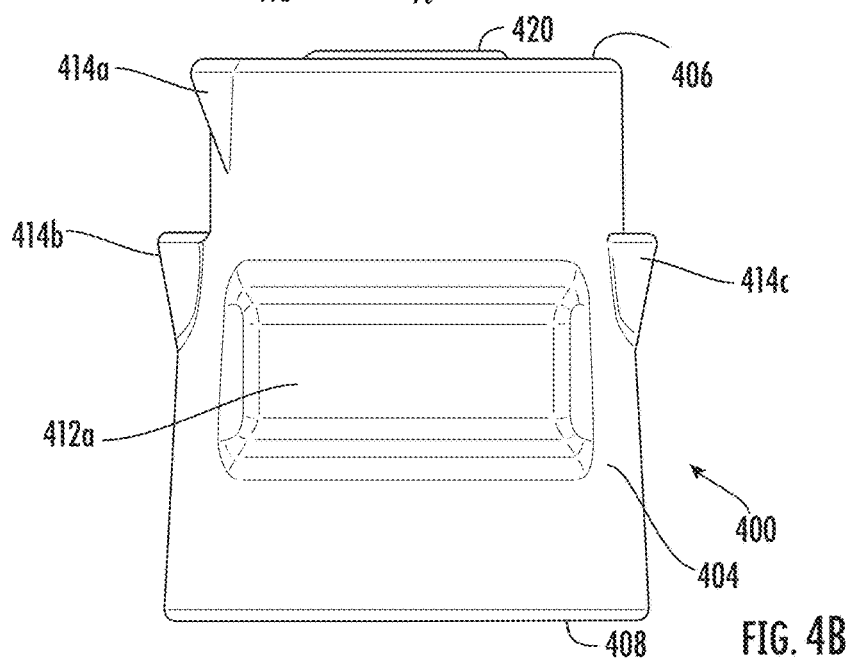
FIG. 4B illustrates a side view of the valve of FIG. 4A.
Figure 4C:
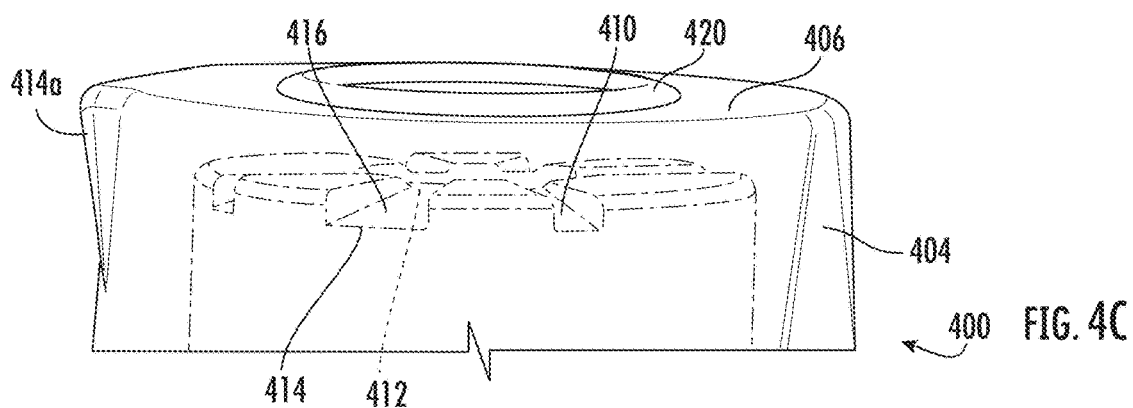
FIG. 4C illustrates a translucent substantially side-view of the valve of FIGS. 4A and 4B.

With reference to FIGS. 4A-4F, an embodiment of a device for providing reinforced sealable access to a working channel is illustrated, which includes a biopsy cap 400 with a tubular body 404 having a proximal end 406, a distal end 408 and extending along a longitudinal axis. The distal end 408 is configured to be installed in-line with the working channel at a proximal end or inlet port of the working channel. The valve 400 includes a substantially linear aperture 402 at the proximal end 406 of the body 404. The aperture 402 extends along a centerline axis r that is perpendicular to a longitudinal axis of the tubular body 404 and is configured to allow one or more medical instruments to be passed therethrough and, at the same time, substantially seal against fluids from the working channel passing therethrough. Six reinforcing ribs 410 are arrayed about the aperture 402. The ribs 410, shown from a bottom view of the valve 400 in FIG. 4A, are disposed on and extend distally along the longitudinal axis from a surface 418 that is internal to the tubular body 404. The ribs 410 extend in a plane substantially perpendicular to the longitudinal axis. The ribs 410 that are farthest away from the normal axis n may be arranged about 45° from the normal axis n or the axis r. The ribs 410 act to reinforce the aperture 402 in the closed position assisting the aperture 402 to resist fluid pressure and exchange across the aperture 402. The arrangement and number of the ribs 410 closer to the axis n increase stiffness of the valve 400 along the axis n relative to the stiffness of the valve along the axis r. This increased stiffness along the axis n (compared to a stiffness along the r axis) also assists in providing a resistive force f along axis n. Resistive force f may be described as a force vector acting in a direction perpendicular to the axis r. The resistive force f may resist a force created by an object (e.g., a guidewire or another instrument being passed through the valve 402). There are also no ribs 410 arranged and extending substantially along the axis r. This is done as well to promote stiffness and closure of aperture 402 of the valve substantially along the direction of axis n relative to the stiffness and closure of the aperture 402 along the axis r. Any forces (e.g., as applied by a guidewire or an instrument) substantially along the axis n that may cause opening and/or tearing of the aperture 402 will engage with portions of the valve 400 having a greater stiffness when compared to portions of the valve 400 that forces may engage substantially along the axis r. As the ribs 410 extend radially away from the aperture 402 from a first end 412 to a second end 414, they become wider and thicker (i.e., the ribs 410 are wider and thicker at the second end 414 than they are at the first end 412). The wider and thicker second ends 414 of the ribs 410 extending toward the aperture 402 to the narrower and thinner first ends 412 contributes to the focused resistive force vectors f directed at the center of the aperture 402 when compared to uniform width and thickness ribs 410. Additionally, specific ribs 416 of the groups of ribs 410 that are normal to the r axis and extend along the normal axis n are wider than the remaining ribs 410 that are offset from the normal axis n. Because ribs 416 are wider than the remaining ribs 410, they have more volume of material to contribute to the resistive force vectors f in the direction perpendicular to the axis r to promote stiffness and closure of the aperture 402. Increasing a combined volume of the material of the ribs, e.g., by increasing the width, thickness, or length of one or more ribs 410, or increasing the number and/or arrangement of ribs 410 in relation to the axis n can contribute to the resistive force vectors f by providing additional rib(s) 410 mass in opposition to the force of an instrument in the aperture 402. These characteristics of the ribs 410 may be adjusted to "tune" the valve 400 to a desired level of resistance to tearing, aperture 402 closure promotion, amount of fluid exchange, and instrument force necessary to pass an instrument through the aperture 402. A rib 410 extending along axis n may contribute to the resistive force vector f more than another rib that is offset from axis n, e.g., a rib 410 that is angled 45° away from axis n about the longitudinal axis of the valve 400. A force required to tear the aperture 402 of the valve 400 having the ribs 410 is greater than the tear force for the same aperture without the ribs 410. Although FIGS. 4A and 4C illustrate six ribs, any number of ribs may be included (e.g., 1, 2, 3, 4, 5, 7, 8, 9, 10, 12, 20, 50, 100, etc.). Although these figures illustrate variable width and thicknesses amongst the ribs 410, the ribs 410 may be of uniform width and thickness. The ribs 410 are arranged substantially symmetrical about the axis r such that the resistive force vectors f acting on aperture 402 are substantially symmetrical. In some embodiments, the arrangement may be asymmetrical. A ridge 420 is also included as will be described below to assist with reinforcement and resisting tears. The ridge 420 may be combined with the valve 400 or a valve 400 may not include the ridge 420. The ridge 420 may be disposed radially outside of the ribs 410 or the ridge may extend through the ribs 410 (e.g., as shown in FIG. 10 discussed below). The ridge 420 and/or ribs 410 may alternatively or additionally be disposed on proximal and/or distal surfaces of a biopsy cap 400.

Figure 4D:
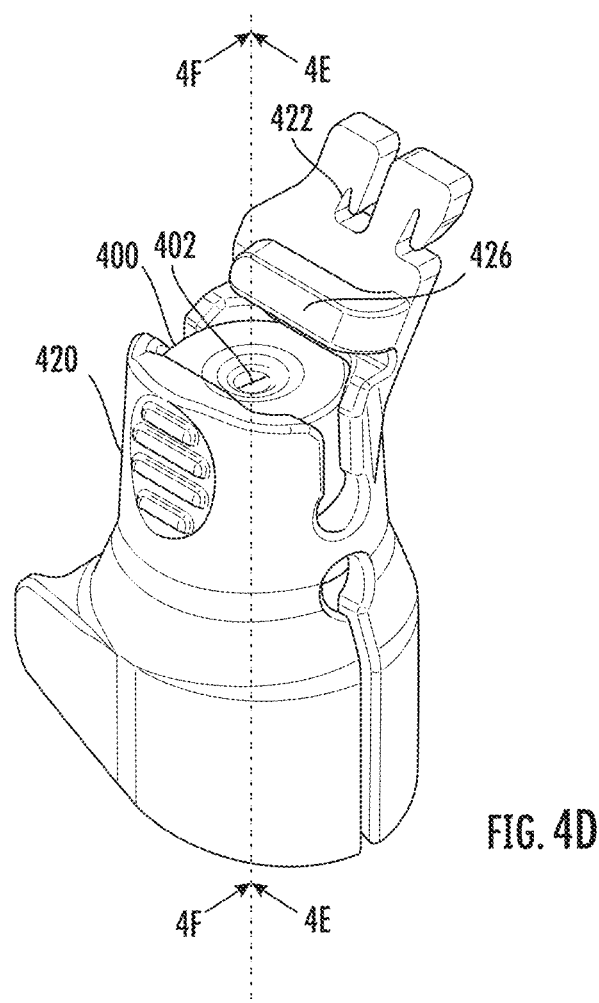
FIG. 4D illustrates an isometric view of the valve of FIGS. 4A-4C in a housing, according to an embodiment of the present disclosure.
Figure 4E:
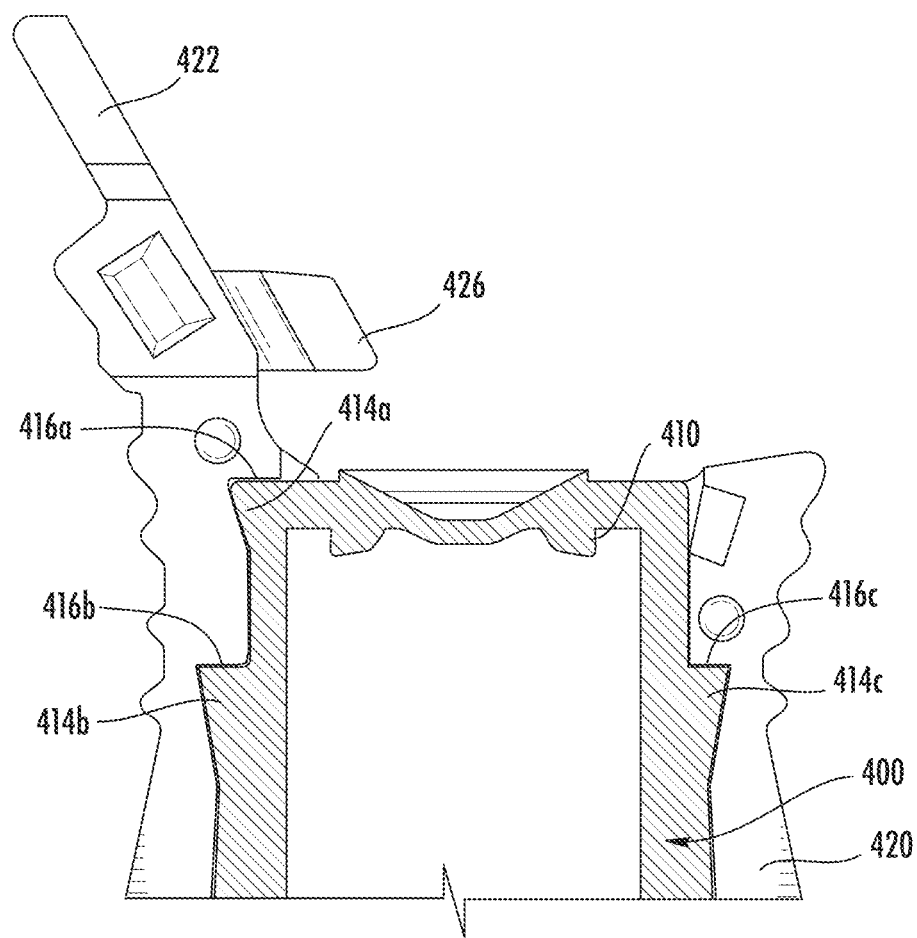
FIG. 4E illustrates a cross-sectional view of FIG. 4D.
Figure 4F:
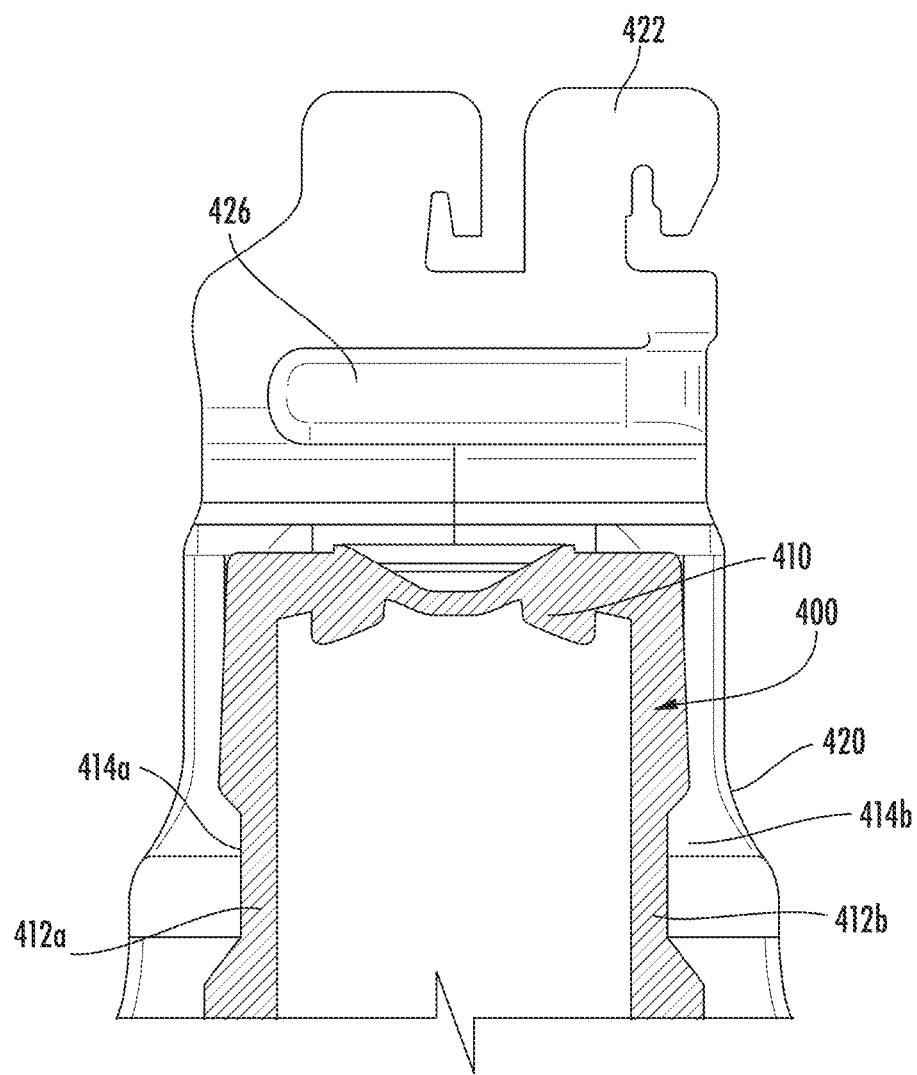
FIG. 4F illustrates a cross-sectional view of FIG. 4D.

With reference to FIGS. 4D-4F, a biopsy cap 400 is illustrated within an exemplary housing 420 according to an embodiment of the present disclosure. The housing 420 includes variable-sized locking channels 422 for accommodating one or more medical instruments (e.g., a guidewire). Medical instruments may also be assisted by the guide arm 426. The biopsy cap 400 also includes a first surface feature 414a attached to or integrally formed with a proximal end of the biopsy cap 400 and second and third surface features 414b, 414c attached to or integrally formed with the tubular body 404 of the biopsy cap 400. These surface features 414a, 414b, and 414c are compressingly and/or frictionally engaging corresponding surface features 416a, 416b, 416c of the housing 420 that may be a lip, a step feature, or the like, that are integrally formed with an inner wall of the housing 420. Recessed portions 412a, 412b are integrally formed within the tubular body 404 of the biopsy cap 400 and are offset from the surface features 414b, 414c by about 90-degrees relative to an outer circumference of the biopsy cap 400. Pivot members 414a, 414b (e.g., first pivot button, first pivot feature, etc.) are integrally formed within the housing 420 and compressingly and/or frictionally engage the corresponding recessed portions 412a, 412b.

In various of the embodiments described here and otherwise, ribs of a device may extend radially in a plane substantially transverse to the longitudinal axis of the device. Each rib of a plurality of ribs may have a width dimension in the transverse plane, and a thickness dimension in a plane substantially parallel to the longitudinal axis. One or more of the ribs may extend substantially perpendicular to the aperture of the device. Some ribs may extend substantially perpendicular to the aperture that have a greater width than the width of any other ribs. The ribs may have a greater width and thickness as they extend radially away from the aperture. The ribs may continuously increase in width and thickness as they extend radially away from the aperture. One or more of the ribs may have a greater thickness than the thickness of one or more of the other ribs, as described above. The body may be hollow, and the ribs may be disposed on a surface internal to the tubular body. Ribs may be arranged just the top surface, on just the bottom surface or both the top and bottom surfaces. The ribs may be arranged symmetrically in a circular pattern around the aperture in a plane that is transverse to the longitudinal axis of the device, as described above. Ribs may be combined with other reinforcing features described herein, such as, for example, a ridge.

Figure 5A:
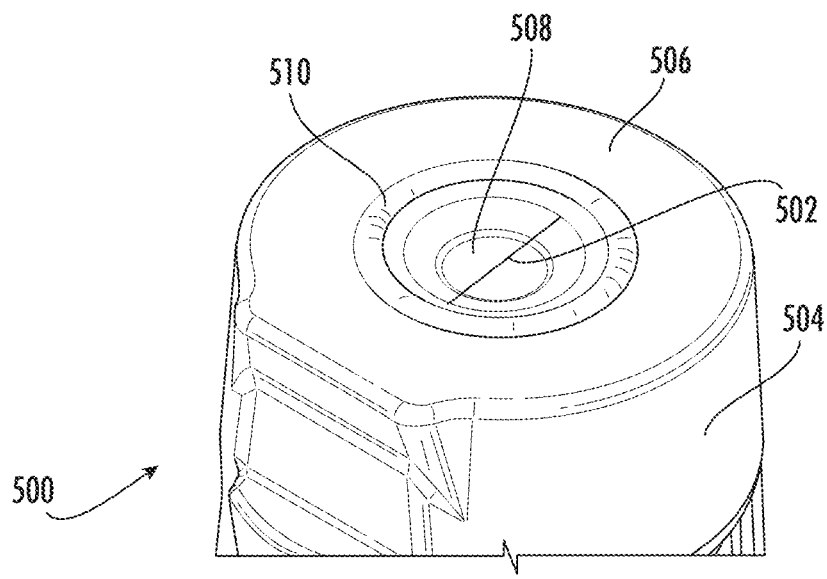
FIG. 5A illustrates an isometric view of a valve including a ridge, according to an embodiment of the present disclosure.
Figure 5B:
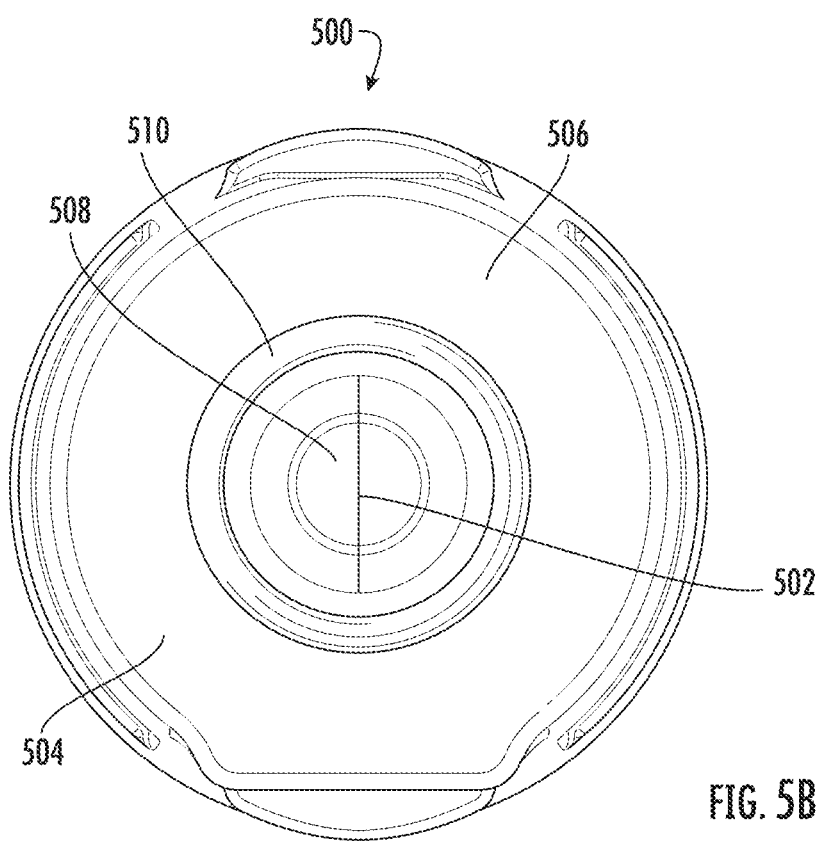
FIG. 5B illustrates a top view of the valve of FIG. 5A.

With reference to FIGS. 5A and 5B, an embodiment of a device for providing reinforced sealable access to a working channel is illustrated, which includes a biopsy cap 500 with a tubular body 504 having a closed substantially linear aperture 502 at a proximal end 506 of the body configured to allow one or more medical instruments to be passed therethrough and, at the same time, substantially seal against fluids from the working channel passing therethrough. The distal end of the body 504 (opposing the proximal end 506) is configured to be installed in-line with the working channel at a proximal end or inlet port of the working channel. A ridge 510 is disposed on the proximal end 506 of the body 504 that extends about the aperture 502. The ridge 510 has a perimeter outline about the aperture 502 that is circular in shape, but may be any shape, e.g., ellipsoidal, oval, a combination of shapes, etc., to encompass the aperture 502. The ridge 510 has a cross-sectional thickness in a plane parallel to a longitudinal axis of the device 500 that is thicker than an inner portion 508 centrally within the ridge 510 of the tubular body 504. The thickness of a ridge may be a variety of thicknesses, e.g., the thickness of a ridge 510 may be at least 25% more than a thickness of a wall of the proximal end 506 of the body 504 that the aperture 502 extends through. For example, a ridge may have a peak thickness of about 0.071 inches (about 1.80 millimeters) and a thickness of a wall of the proximal end 506 of the valve 500 that the aperture 502 extends through may be about 0.038 inches (about 0.97 millimeters). The thickness of the ridge 510 provides resistance against a force from a medical instrument against the walls of the aperture 502 that may otherwise tear the aperture 502. A cross-section of the ridge 510 is substantially semi-circular or half-moon in shape, however a multitude of other shapes may be employed, e.g., parabolic, curved, rectangular, tapered, a combination thereof, etc. The aperture 502 does not extend to the ridge 510, allowing for a minimal amount of tearing before the torn aperture 502 propagates to the ridge 510. The spacing between the ends of the aperture 502 and the ridge 510 may allow for a medical device that is almost as large or larger than the aperture 502 to be inserted and passed through the aperture 502 without undesirable resistance. Additionally, spacing between the ends of the aperture 502 and the ridge 510 may assist in preventing propagation of a tear in the aperture 502.

Figure 6A:
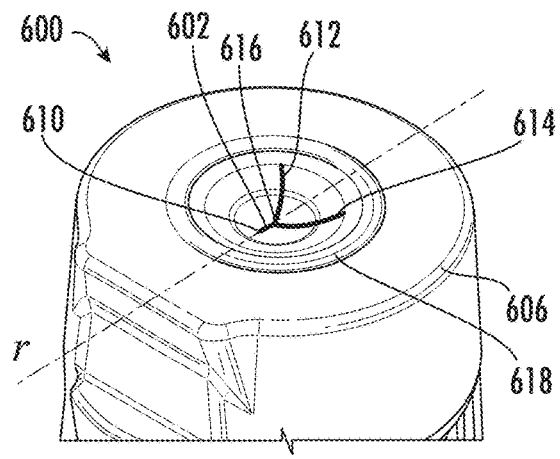
FIG. 6A illustrates an isometric view of a valve including an aperture extending in more than one dimension, according to an embodiment of the present disclosure.
Figure 6B:
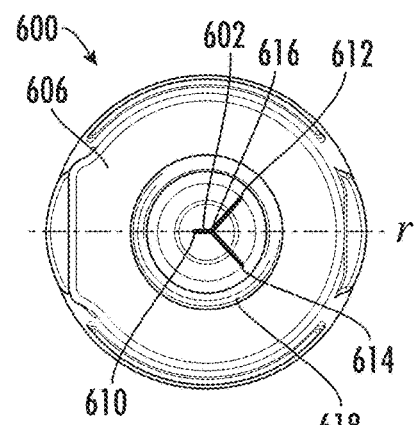
FIG. 6B illustrates a top view of the valve of FIG. 6A.

With reference to FIGS. 6A and 6B, an embodiment of a device for providing reinforced sealable access to a working channel is illustrated, which includes a biopsy cap 600 with a tubular body 600 having a longitudinal axis and an aperture 602 at a proximal end 606 of the body 600. The valve 600 is configured to be installed in-line with the working channel. The aperture 602 is configured to allow one or more medical instruments to be passed therethrough and, at the same time, substantially seal against fluids from the working channel passing therethrough. The aperture 602 has a reinforced pattern that extends in a plane substantially transverse to the longitudinal axis in more than one dimension. The aperture 602 has a first end 610, a second end 612, and a third end 614. The aperture 602 extends substantially linearly from the first end 612 to a split point 616 and continues to extend from the split point 616 separately and substantially linearly to each of the second and third ends 612, 614. This aperture 602 allows for multiple medical instruments to be accepted and fixed into an end 610, 612, 614 of the aperture 602, without multiple instruments occupying the same end 610, 612, 614, which may reduce tearing of the aperture 602 as will be discussed below with reference to FIGS. 7 and 8 and above with reference to FIGS. 1-3B. Although the portions of the aperture 602 extending from the split point 616 to each of the second and third ends 612, 614 are substantially the same length and extend at substantially the same angle degree from the split point 616 to the first end and from an axis r of the aperture 602, these angles and lengths may be variable, or some combination of uniform and variable among the ends. The angles may be such that the portions of the aperture 602 extending from the split point 616 to each of the second and third ends 612, 614 are oriented toward a locking channel configured to fix a medical device within the aperture 602. Additionally, although three ends 610, 612, and 614 are illustrated, any number of ends may be employed, e.g., a number of ends equivalent to a number of medical instruments to fix into a position. Although the portions of the aperture 602 extending from the split point 616 to the second and third ends 612, 614 are longer than the portion of the aperture 602 extending from the first end 610 to the split point 616, these portions may be variable in length relative to each other or may be substantially equivalent. The second and third ends 612, 614 may be configured to each accommodate a single guidewire with substantially no tearing. An exemplary diameter of a guidewire may range from about 0.025 inches (about 0.635 millimeters) to about 0.038 inches (about 0.965 millimeters), and an exemplary length of the aperture 602 from the first end 610, along the axis r, to the split point 616 may be about 0.040 inches (1.016 millimeters) while a greater length may be used to accommodate multiple guidewires, multiple instruments, and/or larger instruments through the aperture 602. An exemplary length of the aperture 602 from the split point 616, to the second end 612 or to the third end 614 may be about 0.040 inches (1.016 millimeters) and may be less than about 0.050 inches (1.27 millimeters). A length of the aperture 602 from the first end 610, along the axis r, to a point between the second end 612 and the third end 614 may be about 0.080 inches (2.032 millimeters) to about 0.140 inches (3.556 millimeters). Although a ridge 618 is illustrated about the aperture 602 that is similar to the ridge 510 discussed with respect to FIGS. 5A and 5B, various embodiments may include or exclude the ridge 618.

Figure 7:
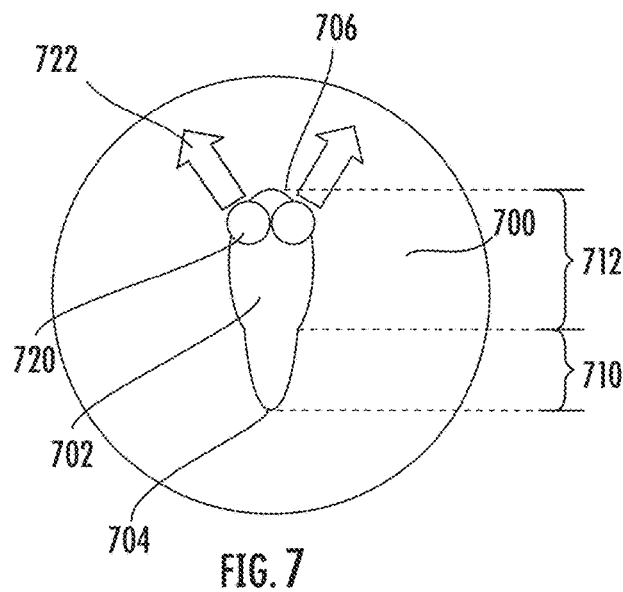
FIG. 7 illustrates a top view of a valve.

With reference to FIG. 7, a top view of a biopsy cap 700 is illustrated, which includes a substantially linear aperture 702 extending from a first end 704 to a second end 706. Two medical instruments 720 (e.g., guidewires) extend through the aperture 702 at the second end 706 and are forced against the walls of the aperture 702 in the general direction of the vectors 722 (e.g., during and after fixing the medical instruments 720 into locking channels). The substantially linear aperture 702 is opened at a first portion 710 near the first end 704 and is torn open at a second portion 712 near the second end. This tearing and opening in FIG. 7 have opened the aperture 702 to a larger gap space than any gap space that is illustrated in FIG. 2, which is a substantially linear tear that extends along the aperture 202 of FIG. 2. The aperture 702 is torn similarly to what is described with reference to the similar valve in FIGS. 3A and 3B above.

Figure 8:
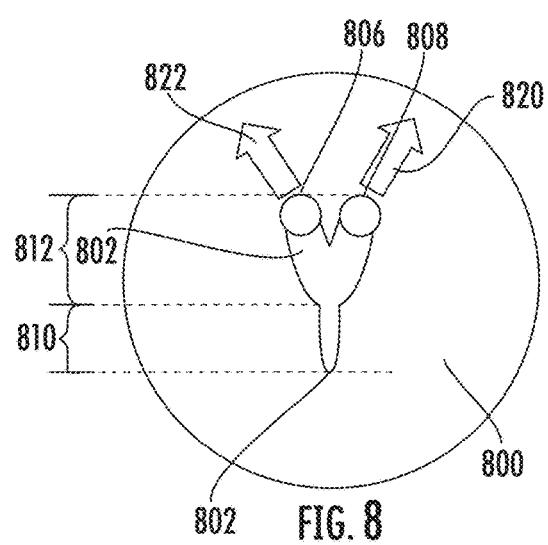
FIG. 8 illustrates a top view of a valve including an aperture extending in more than one dimension, according to an embodiment of the present disclosure.

With reference to FIG. 8, a top view of an embodiment of a device for providing reinforced sealable access to a working channel is illustrated, which includes a biopsy cap 800 with an aperture 802 that has a reinforced pattern that extends in a plane substantially transverse to the longitudinal axis of the device in more than one dimension. Similar to the illustration and discussion of FIGS. 6A and 6B above, the aperture 802 extends from a first end 804 to a split point and thereafter extends to each of a second end 806 and a third end 808. Two medical instruments 820 (e.g., guidewires) extend through the aperture 802, one at each of the second end 806 and the third end 808. The medical instruments 820 are forced against the walls of the aperture 802 in the general direction of the vectors 822 (e.g., during and after fixing the medical instruments 820 into locking channels).

Comparing the force vectors 722, 822 and tearing in FIGS. 7 and 8, tearing has opened the apertures 702, 802 to more than what is illustrated in FIG. 2, which is substantially a linear tear that extends along the aperture 202 of FIG. 2. The substantially linear apertures 702, 802 of FIGS. 7 and 8 are torn and/or opened at both a first portion 710, 810 near the first ends 704, 804 and at a second portion 712, 812 near the opposing ends (second ends 706, 806 and third end 808). Because the reinforced pattern aperture 802 of FIG. 8, according to an embodiment of the present disclosure, includes a separate second and third end 806, 808 for each of the medical devices 820, the aperture 802 may tear substantially linearly along the directions of the second end 806 and third end 808, resulting in open areas of the first portion 810 and second portion 812 of FIG. 8, which are smaller than the open areas of the first portion 710 and second portion 712 of FIG. 7 respectively, where there is not a reinforced pattern to the aperture. These smaller open areas of the portions 810, 812 of FIG. 8 when compared to the open areas of the portions 710, 712 of FIG. 7, allow for a better seal against the exchange of fluids across the aperture 802 when instruments are passed therethrough.

Figure 9:
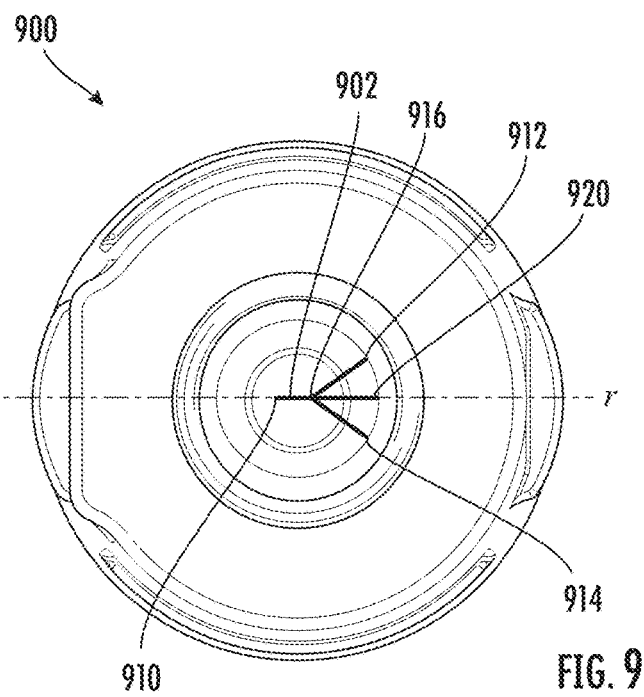
FIG. 9 illustrates a top view of a valve including an aperture extending in more than one dimension, according to an embodiment of the present disclosure.

FIG. 9 illustrates a top view of a valve 900 including an aperture extending in more than one dimension, according to an embodiment of the present disclosure. The embodiment of FIG. 9 is the same as that of FIGS. 6A and 6B having an aperture 902 that also includes a fourth end 920. The fourth end 920 extends opposite the first end 910 and extends from the split point 916 and substantially along the axis r, and is between the second and third ends 912, 914. The fourth end 920 may accommodate an additional guidewire and/or may assist with passability of a medical device.

Figure 10A:
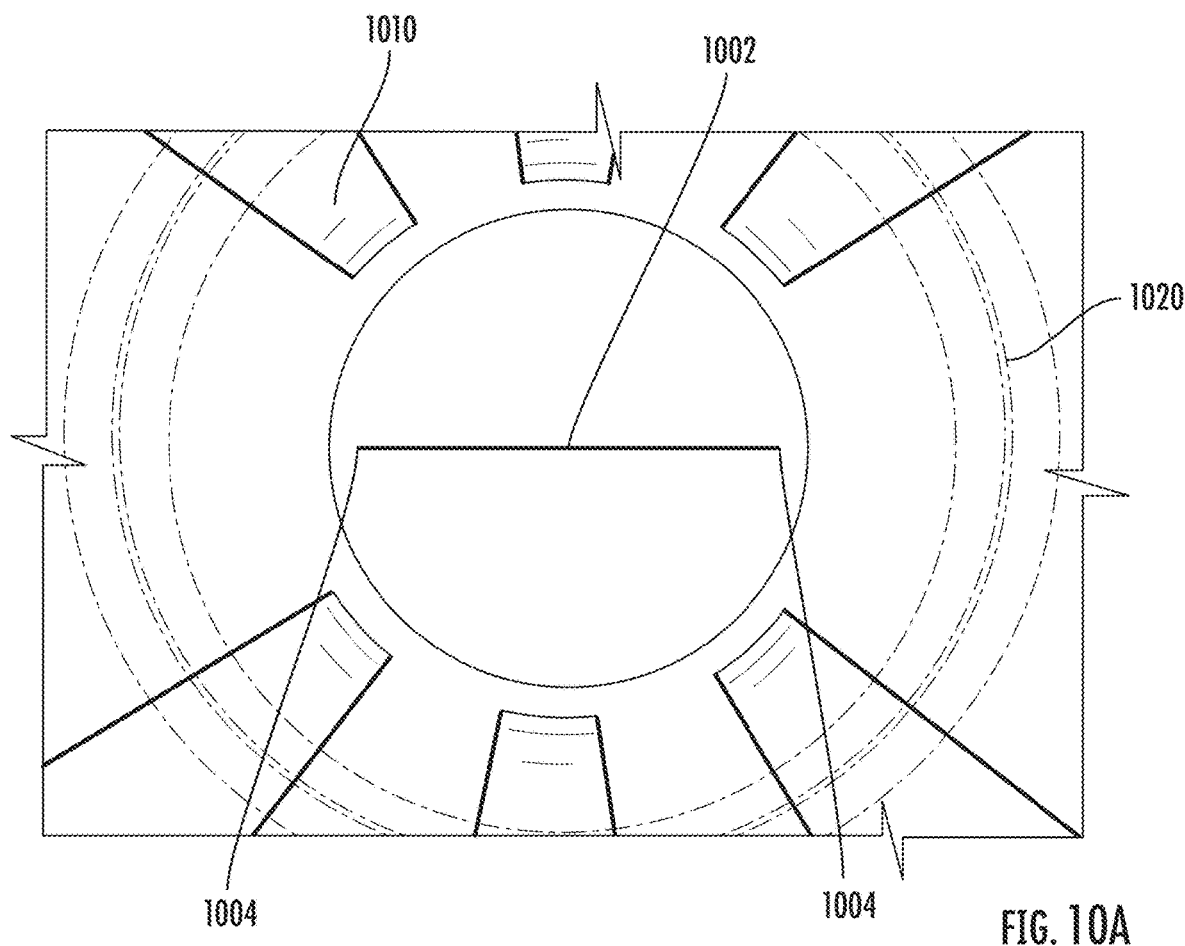
FIG. 10A illustrates a magnified view of a working channel side of an aperture of a valve, according to an embodiment of the present disclosure.
Figure 10B:
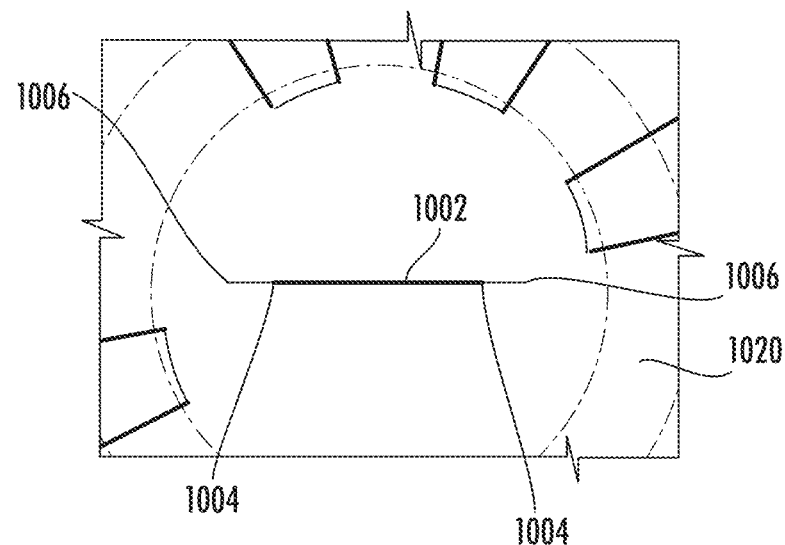
FIG. 10B illustrates a magnified view of a working channel side of an aperture of a used valve, according to an embodiment of the present disclosure.
Figure 10C:
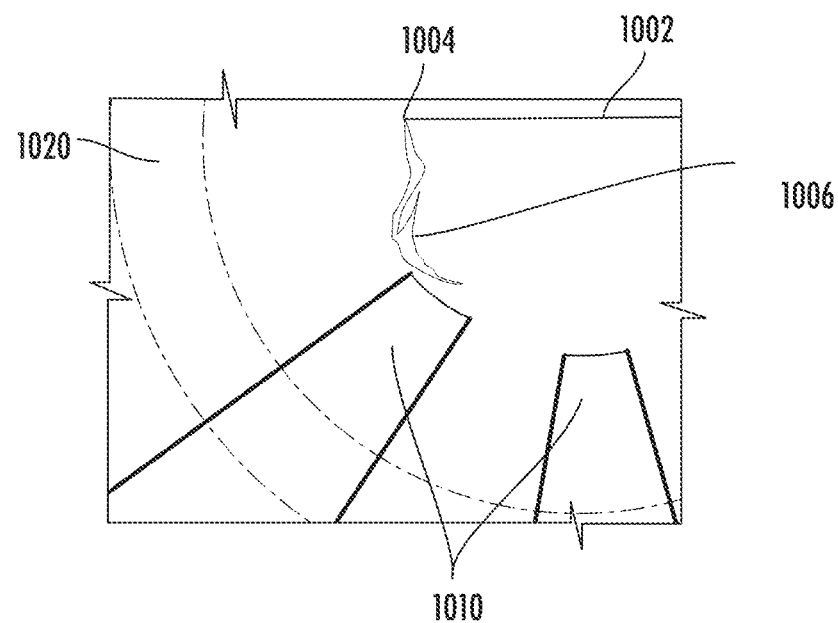
FIG. 10C illustrates a magnified view of a working channel side of an aperture of a used valve, according to an embodiment of the present disclosure.

FIGS. 10A-10C illustrate magnified views of valves, according to embodiments of the present disclosure. An aperture 1002 of the valves extend substantially linearly across a portion of the valve. The aperture 1002 has a length between the ends 1004 of the aperture. During use of a valve, one or more medical instruments may be inserted through the aperture 1002, which may cause tearing. Tearing may be limited or tearing propagation may be reduced by the ribs 1010 and ridge 1020 as described herein. With reference to FIG. 10A, the aperture 1002 of a valve including ribs 1010 and a ridge 1020 has not experienced any tearing after use. With reference to FIG. 10B, the original length of the aperture 1002 between the ends 1004 has been torn to a larger-sized aperture between the torn ends 1006, but the tearing has not propagated in a manner so-as to affect the functionality of the valve. The original aperture 1002 length of FIG. 10B (between the ends 1004) may be about 1.5 mm to about 4 mm, while the torn aperture 1002 length (between the torn ends 1006) may be at least about 5 mm. With reference to FIG. 10C, an aperture 1002 may tear toward a torn end 1006 having a tear path that is substantially non-linear with the aperture 1002 (i.e., along a line between the original ends 1004). The non-linear tear end 1006 is maintained radially within the ridge 1020 and also radially within the ribs 1010.

In various embodiments, an aperture of a valve may not extend entirely through a wall of the valve. An aperture may terminate at a certain distance within a thickness of a wall of a valve, so that the remaining thickness of the wall at the aperture may be punctured through by a medical instrument in use. Alternatively, an aperture may be covered by a membrane that may be adhered to the wall of a valve such that it is disposed across the aperture before it is punctured by a medical instrument in use.

In various embodiments, a length or portions of a length of an aperture may range from about 2 mm to about 5 mm, about 1.5 mm to about 4 mm, about 3 mm, etc. A length of a portion having an end of a "Y-shaped" aperture may be about 3 mm. The length of a tear propagating from an aperture may compromise the functionality of a valve depending on the length of the aperture. For example, a medical instrument causing a tear having a length of about 10% of the length of an aperture may be significant enough to affect the performance of the valve.

In various embodiments, a valve may comprise flexible materials such as silicone, liquid silicone rubber, rubber, polymer, elastomer, thermoplastic elastomer (TPE), flexible plastic, or combinations thereof. Variable thicknesses across the valve may be employed for various functions, e.g., a thicker body for installing securely in-line with a working channel, a thinner wall about an aperture for passage of medical devices, a thicker ridge about an aperture to prevent extended tearing, thicker rib portions to assist in maintaining a closed position of an aperture, or the like.

In various embodiments, a valve may be molded into a tubular body to make up a formation or shape that is configured or customized to be installed into a particular housing and/or be compatible with a particular working channel. A patterned aperture according to the embodiments described here or otherwise according to the present disclosure may be cut into the formation.

All of the devices and/or methods disclosed and claimed herein can be made and executed without undue experimentation in light of the present disclosure. While the devices and methods of this disclosure have been described in terms of preferred embodiments, it may be apparent to those of skill in the art that variations can be applied to the devices and/or methods and in the steps or in the sequence of steps of the method described herein without departing from the concept, spirit and scope of the disclosure. All such similar substitutes and modifications apparent to those skilled in the art are deemed to be within the spirit, scope and concept of the disclosure as defined by the appended claims.

What is claimed is:

1. A device for providing reinforced sealable access to a working channel, the device comprising:
   a tubular body having a proximal end, a distal end, and a longitudinal axis, the distal end configured to be removably disposed on a proximal end of the working channel in fluid communication therewith;

an elongated aperture at the proximal end of the body extending along a slit axis and configured to allow one or more medical instruments to be passed therethrough and, at the same time, substantially seal against fluids from the working channel passing therethrough; and a plurality of reinforcing ribs on each side of the aperture, each reinforcing rib extending along a radius from a center of the aperture to reinforce the aperture against tearing, wherein each reinforcing rib extends 45° or closer to an axis normal to the slit axis and extending along a diameter of the body.

2. The device of claim 1, further comprising one or more reinforcing ribs extending substantially perpendicular to the slit axis.

3. The device of claim 1, wherein the reinforcing ribs extending furthest from an axis normal to the slit axis and through the center of the aperture are about 45° from the slit axis.

4. The device of claim 1, wherein the reinforcing ribs include at least one perpendicular reinforcing rib extending perpendicular to the slit axis, and at least one reinforcing rib about 45° from the perpendicular reinforcing rib on each side of the perpendicular reinforcing rib.

5. The device of claim 1, wherein none of the reinforcing ribs extends along the slit axis.

6. The device of claim 1, wherein the reinforcing ribs extend radially in a plane substantially perpendicular to the longitudinal axis.

7. The device of claim 1, wherein the reinforcing ribs continuously increase in width and thickness as they extend radially away from the aperture.

8. The device of claim 1, wherein reinforcing ribs extending substantially perpendicular to the aperture have a greater width than the width of reinforcing ribs not extending substantially perpendicular to the aperture.

9. The device of claim 1, wherein one or more of the reinforcing ribs has a greater thickness than the thickness of one or more of the other of the reinforcing ribs.

10. The device of claim 1, wherein the tubular body is hollow, and the reinforcing ribs are disposed on a surface internal to the hollow tubular body.

11. The device of claim 1, wherein a force required to tear the aperture is greater than a force required to tear the aperture without the reinforcing ribs.

12. The device of claim 1, wherein the plurality of reinforcing ribs extend on a distal surface of the proximal end of the body that is internal to the tubular body.

13. The device of claim 1, wherein the aperture extends along a centerline axis perpendicular to the longitudinal axis of the body.

14. A device for providing reinforced sealable access to a working channel, the device comprising:
a tubular body having a proximal end, a distal end, and a longitudinal axis, wherein the distal end is configured to be removably disposed on a proximal end of the working channel in fluid communication therewith;

a substantially linear aperture at the proximal end of the body extending along a slit axis and configured to allow one or more medical instruments to be passed therethrough and, at the same time, substantially seal against fluids from the working channel passing therethrough; and a first reinforcing rib extending substantially perpendicular to the aperture in a first direction away from a first side of the aperture and along an axis normal to the slit axis and extending along a diameter of the body; and a second reinforcing rib extending substantially perpendicular to the aperture in a second direction opposite the first direction and away from a second side of the aperture and along an axis normal to the slit axis and extending along a diameter of the body.

15. The device of claim 14, further comprising additional reinforcing ribs extending away from the first side of the aperture.

16. The device of claim 15, wherein the additional reinforcing ribs extend no more than 45° from the first reinforcing rib.

17. The device of claim 15, further comprising additional reinforcing ribs and away from the second side of the aperture.

18. The device of claim 17, wherein the additional reinforcing ribs extending away from the first side of the aperture extend no more than 45° from the first reinforcing rib, and the additional reinforcing ribs extending away from the second side of the aperture extend no more than 45° from the second reinforcing rib.

19. A device for providing reinforced sealable access to a working channel, the device comprising:
a tubular body having a proximal end, a distal end, a longitudinal axis, and an outer perimeter extending about the longitudinal axis, wherein the distal end is configured to be removably disposed on a proximal end of the working channel in fluid communication therewith;

an elongated aperture at the proximal end of the tubular body configured to allow more than one medical instrument to be passed therethrough at the same time and resisting tearing while substantially sealing against fluids from the working channel passing therethrough;

a plurality of reinforcing ribs extending along a direction transverse to the aperture to reinforce the aperture against tearing; and a reinforcing ridge on the proximal end of the tubular body extending circumferentially about the elongated aperture and the reinforcing ribs to reinforce the elongated aperture against tearing, the reinforcing ridge being spaced inwardly of the outer perimeter of the tubular body and spaced outwardly from the elongated aperture and the reinforcing ribs.

20. The device of claim 19, wherein the reinforcing ribs continuously increase in width in a direction transverse to the longitudinal axis as they extend radially away from a center of the aperture.

* * * * *